(12) United States Patent
Littleton

(10) Patent No.: US 9,127,985 B2
(45) Date of Patent: Sep. 8, 2015

(54) METHOD AND APPARATUS FOR NON-RESONANT BACKGROUND REDUCTION IN COHERENT ANTI-STOKES RAMAN SCATTERING (CARS) SPECTROSCOPY

(75) Inventor: Bradley Neville Littleton, London (GB)

(73) Assignee: King's College London, London (GB)

( * ) Notice: Subject to any disclaimer, the term of this patent is extended or adjusted under 35 U.S.C. 154(b) by 307 days.

(21) Appl. No.: 13/814,417

(22) PCT Filed: Aug. 2, 2011

(86) PCT No.: PCT/GB2011/001161
§ 371 (c)(1),
(2), (4) Date: Apr. 22, 2013

(87) PCT Pub. No.: WO2012/017201
PCT Pub. Date: Feb. 9, 2012

(65) Prior Publication Data
US 2013/0208272 A1 Aug. 15, 2013

(30) Foreign Application Priority Data
Aug. 6, 2010 (GB) .................................. 1013321.3

(51) Int. Cl.
*G01J 3/44* (2006.01)
*G01N 21/65* (2006.01)

(52) U.S. Cl.
CPC . *G01J 3/44* (2013.01); *G01N 21/65* (2013.01); *G01N 2021/653* (2013.01)

(58) Field of Classification Search
CPC ...... G01N 2021/653; G01N 21/65; G01J 3/44
See application file for complete search history.

(56) References Cited

U.S. PATENT DOCUMENTS 6,798,507 B2   9/2004   Xie et al.
7,388,668 B2   6/2008   Potma et al.
(Continued)

FOREIGN PATENT DOCUMENTS

JP   2004-534232   11/2004
JP   2008-502915    1/2008
(Continued)

OTHER PUBLICATIONS

Jurna et al., "Background Free CARS Imaging by Local Phase Detection", 2009, SPIE, vol. 7183, pp. 1-7.*
(Continued)

*Primary Examiner* — Kara E Geisel
(74) *Attorney, Agent, or Firm* — Klarquist Sparkman, LLP

(57) ABSTRACT

Embodiments of the invention provide a simple and robust system that allows non-resonant background to be removed from anti-Stokes signals generated during coherent anti-Stokes Raman spectroscopy (CARS) even when using cheaper laser systems, which do not have transform limited pulses. In particular, resonant CARS signals have a real and imaginary component. The imaginary component is directly related to the spontaneous Raman spectrum, for which there are already large spectral databases to allow chemical identification. The NRB signal, on the other hand, only has a real component. Within embodiments of the invention we recover the imaginary component of the entire CARS signal by simultaneously generating two CARS signals at orthogonal polarisations: one has the imaginary components destructively interfering with (i.e. subtracted from) the real components, the other has them constructively interfering. Measuring these two polarisations and subtracting them therefore cancels out the real part of the signal, leaving only the imaginary components.

24 Claims, 3 Drawing Sheets

(56) References Cited

U.S. PATENT DOCUMENTS

| | | |
|---|---|---|
| 8,482,738 B2 | 7/2013 | Rimke et al. |
| 2003/0011765 A1* | 1/2003 | Xie et al. ............... 356/301 |
| 2004/0145735 A1 | 7/2004 | Silberberg et al. |
| 2005/0280827 A1 | 12/2005 | Potma et al. |
| 2008/0304047 A1* | 12/2008 | Lee et al. ............... 356/51 |

FOREIGN PATENT DOCUMENTS

| | | |
|---|---|---|
| JP | 2010-526345 | 7/2010 |
| JP | 2011-175093 | 9/2011 |
| WO | WO 03/004983 | 1/2003 |

OTHER PUBLICATIONS

Gachet et al., "Background-free Coherent Anti-Stokes Raman Spectroscopy Near Transverse Interfaces: a Vectorial Study", 2008, Optical Society of America, vol. 25, No. 10, pp. 1655-1666.*

Chen et al., "Optimal Laser Pulse Shaping for Interferometric Multiplex Coherent Anti-Stokes Raman Scattering Microscopy," *Journal of Physical Chemistry*, vol. 112, No. 12, pp. 3653-3661 (Feb. 2008).

Lepetit et al., "Linear techniques of phase measurement by femtosecond spectral interferometry for applications in spectroscopy," *J. Opt. Soc. Am. B*, vol. 12, No. 12, pp. 2467-2474 (Dec. 1995).

Lim et al., "Single-pulse phase-control interferometric coherent anti-Stokes Raman scattering spectroscopy," *Physical Review A*, vol. 72, 4 pp. (Oct. 2005).

Search Report dated Oct. 22, 2010, from Great Britain Application No. 1013321.3, 3 pp.

Volkmer, "Vibrational imaging and microspectroscopies based on coherent anti-Stokes Raman scattering microscopy," *Journal of Physics D: Applied Physics*, pp. R59-R81 (Feb. 2005).

Evans et al., "Coherent anti-Stokes Raman scattering spectral interferometry: determination of the real and imaginary components of nonlinear susceptibility chi(3) for vibrational microscopy," *Optics Letters*, vol. 29, No. 24, pp. 2923-2925 (Jan. 2004).

International Search Report dated Nov. 2, 2011, from International Application No. PCT/GB2011/001161, 4 pp.

Lim et al., "Single pulse interferometric coherent anti-Stokes Raman scattering (CARS)," *SPIE Proc.*, vol. 6442, pp. 644205-1-644205-10 (Jan. 2007).

Lu et al., "Elliptically polarized coherent anti-Stokes Raman scattering microscopy," *Optics Letters*, vol. 33, No. 23, pp. 2842-2844 (Dec. 2008).

Vestin et al., "Development of rotational CARS for combustion diagnostics using a polarization approach," *Proc. of the Combustion Institute*, vol. 31, No. 1, pp. 833-840 (Dec. 2006).

Written Opinion dated Nov. 2, 2011, from International Application No. PCT/GB2011/001161, 5 pp.

Notice of Reason for Rejection dated Jun. 30, 2015, from Japanese Patent Application No. 2013-523657, 6 pp.

* cited by examiner

METHOD AND APPARATUS FOR NON-RESONANT BACKGROUND REDUCTION IN COHERENT ANTI-STOKES RAMAN SCATTERING (CARS) SPECTROSCOPY

CROSS REFERENCE TO RELATED APPLICATIONS

This application is the U.S. National Stage of International Application No. PCT/GB 2011/001161, filed Aug. 2,2011, which was published in English under PCT Article 21(2), which in turn claims the benefit of GB Application No. 1013321.3, filed Aug. 6, 2010. The provisional application is incorporated herein in its entirety.

TECHNICAL FIELD

The present invention relates to a method and apparatus for reducing or eliminating the non-sonant background obtained during Coherent anti-Stokes Raman Scattering (CARS) spectroscopy.

BACKGROUND TO THE INVENTION

CARS is a $3^{rd}$ order non-linear optical interaction that has been used for chemical analysis, combustion and flow diagnostics, and is now being applied (by many different groups worldwide) to biological microscopy. CARS signals are always generated in concert with non-resonant background (NRB).

Fluorescence microscopy has allowed a great deal of cell structure and function to be studied, but it has some inherent drawbacks. It relies on tagging proteins with fluorescent dyes or genetically encoded fluorescent proteins, which can alter the targeted protein functions. Furthermore, fluorescent dyes bleach under illumination, which limits sensitivity and creates reactive species in the cell. CARS avoids these problems: it does not cause bleaching, as it is a parametric process which leaves no energy in the target molecule; and the signal depends on vibrational resonances, so it allows chemical species to be identified without tagging. There has therefore been an intense research effort over the last decade exploring the application of CARS to microscopy.

However, CARS has some drawbacks of its own. It is more complex to implement than fluorescence, as three beams (called the pump, probe and Stokes beams) of at least two different frequencies must be combined in the sample to generate the fourth, anti-Stokes, beam. Also, all media have a third order non-linear optical response, so the resonant signal is always generated along with a non-resonant background signal (NRB). As CARS is a coherent process the two signals are not simply additive; they will add and subtract depending on their relative phase. This distorts line shapes and makes spectral analysis difficult. Also, CARS requires pulsed lasers with high peak energies, and under these conditions the NRB becomes large, obscuring weak resonant signals. As a consequence, much of the research into CARS microscopy has been directed at developing ways to remove the NRB.

Most of the CARS microscopy studies to date have looked at lipid rich structures, as the high density of C-H vibrations gives strong signals that can be distinguished against the NRB. However, the line distortion and decreased signal-to-background due to NRB has so far prevented full realisation of the initial promise of CARS microscopy: that is, chemical specificity without tagging (as in spontaneous Raman scattering).

Despite CARS being a very useful technique in biology, the vast majority of CARS microscopes in use today are hand-built systems: complexity, expense and the specialist expertise required to operate them has (until recently) hindered development of a commercial product. Existing NRB removal schemes require expensive laser systems with near transform limited pulses, along with complex instruments such as spatial light modulators (SLM's).

PRIOR ART

There are currently many different approaches to NRB removal. They can be grouped into five main classifications (with some overlap between them): polarisation methods, temporal methods, computational techniques, epi-detection, and interferometric methods.

U.S. Pat. No. 6,798,507 B2 describes a polarisation method that attempts to exclude NRB by detecting the CARS signal along the polarisation orthogonal to it. These methods suffer from low signal levels (the resonant signals aren't amplified as in hetero- or homodyne methods) and large linear backgrounds, as imperfections in optics leads to leakage of the NRB into the signal channel. The signal also scales with the square of concentration, which limits sensitivity.

Temporal methods use the fact that the NRB is generated instantaneously by the driving fields, whereas resonant excitations typically persist for several picoseconds. By delaying the probe pulse with respect to the pump and Stokes pulses it is therefore possible to reduce the NRB. These techniques also suffer from low signal levels, as the resonant excitations decay exponentially with time, and the signal depends on the dephasing time of the Raman mode being probed. The signal also scales quadratically with concentration.

Computational techniques attempt to recover the phase of the non-linear response from a raw CARS spectrum, which then allows the separation of the resonant response into its real and imaginary components, and removal of the NRB (which typically only has a real component). These can be broadly grouped into methods that use maximum entropy model determination (Vartiainen et al, *Direct extraction of Raman line -shapes from congested CARS spectra*,Optics Express 14(8):3622-30, 2006), and ones that use Fourier analysis combined with causality conditions (eg Liu et al *Broadband CARS spectral phase retrieval using a time-domain Kramers-Konig transform*, Optics Letters 34(9):1363-5, 2009; and Liu et al *Fast extraction of resonant vibrational response from CARS spectra with arbitrary nonresonant background*, Journal of Raman Spectroscopy 40:726-31, 2009). They all require either independent measurement of NRB (which can change in magnitude and form throughout a sample), or assumptions about its smoothness and strength relative to the resonant components. Large resonant responses aren't correctly recovered, small resonances can be lost, and these techniques break down if fluctuations in the NRB have similar spectral width to resonances in the sample (which is the case for CARS systems based on low-cost supercontinuum sources).

Epi-detected CARS, as described in U.S. Pat. No. 6,809, 814 B2, relies on the fact that, due to the phase matching condition of CARS, signals can only be generated in the backward direction by objects smaller than the wavelength of the input fields. This method gives high contrast, but it is limited to these sub-wavelength objects.

Interferometric methods use the coherent nature of the interaction to exclude NRB. Many of these have the advantage of amplifying the resonant signal by coherent mixing with a local oscillator (LO) field (see e.g. U.S. Pat. No. 7,586, 618 B2, and US 2010/0110426 A1). Usually this has the additional benefit that the anti-Stokes signal then scales linearly with concentration, which makes small signals easier to detect.

The majority of interferometric CARS systems (and in particular, broadband systems) use pulse shaping via spatial light modulators (SLMs). Some suppress the NRB by generating a narrow probe pulse with a π phase step at the spectral peak, while others use spectrally shifted or temporally broadened pulses of opposite phase (see e.g. US 2010/0110426 A1). However, SLM's are complex and expensive, they require expertise to align and use, and their spectral width and resolution is limited by their overall width and pixel size. Furthermore, most of these interferometric systems require transform limited laser pulses. This means that dispersion in other optics in the system must be pre-compensated for, which introduces further complexity. This is particularly problematic for approaches that use ultra fast pulses to give a wide spectral range: as pulses become shorter dispersion becomes much harder to control. This can often be accounted for in the SLM, however this makes the system more complex to operate and means that it must be properly precalibrated before measurements are taken. Ultra fast laser systems with high mode quality outputs tend to be very expensive, and can often require considerable expertise to maintain.

Hetero- and homodyne systems either use the non-resonant background as a LO (see e.g. U.S. Pat. No. 7,586,618 B2 or Lim et al.,*Single-Pulse phase-control nterferometric coherent anti-Stokes Raman scattering spectroscopy*, Physical Review A 72 041803(R), 2005), or one generated externally (see e.g. U.S. Pat. No. 7,586,618 B2 ). An externally generated LO must have a fixed phase over its entire spectral width, which means that dispersion must be carefully compensated for. Such systems also need to be extremely stable between the sample and the medium that generates the LO. Internally generated LO's have the benefit that spectral stability is assured, as all the beams have a common path, and there is no difference between the dispersion experienced by the signal field and the LO. Hetero- and homodyned interferometric systems with an internal LO are therefore the most promising options for robust, high signal, NRB removal.

Of closer background relevance to the present invention is the process of Dual Quadrature Spectral Interferometry (DQSI) described by Lepetit *et al Linear techniques of phase measurement by femtosecond spectral interferometry for applications in spectroscopy*, J. Opt. Soc. Am B, Vol 12, No. 12, December 1995 (and see also U.S. Pat. No. 6,020,963). This is a system for probing the optical response of a medium, by interfering a circularly polarised beam (the reference field) with a linearly polarised one, after the linear beam has passed through, and been affected by, the medium. The resultant beam is split into two orthogonal projections, dispersed in a spectrometer, and imaged onto a detector. One of the measured projections has the reference beam mixed with the real part of the linear polarised beam, while in the other it is mixed with the imaginary part. If the phase of the reference beam is known, this allows both the amplitude and phase of the linearly polarised beam to be determined.

With respect to the possibility of applying the work of Lepetit to CARS, DQSI is arranged in a Mach-Zender interferometer configuration, and, indeed, cannot work in a collinear geometry as the reference pulse must not pass through the object. Such an arrangement is therefore not suited to removing NRB from CARS. In addition, due to the symmetries inherent in CARS, using a circularly polarised pump beam (i.e. φ=45°) gives no information on the imaginary component of the third-order response.

A related piece of prior art is DQSI-CARS, described by Lim et al ibid. In this system, a broadband pulse from an ultra fast laser is processed via a spatial light modulator (SLM), such that a small portion of the short wavelength edge of the pulse is given an orthogonal polarisation, and arbitrary phase. The narrowband portion is the probe beam, and the broadband component serves as both the pump and Stokes beams. The generated polarisation for the probe only has a component orthogonal to the Stokes beam, which can be set to any phase. Detection is performed at ±45° to the pump/Stokes beam. Analysing the data from this system requires that the probe pulse is weak compared to the broadband pulse, in order that two of the components of the third-order response can be ignored, and that the NRB is orientated primarily along the pump/Stokes direction. Note that to efficiently excite CARS using a broadband pulse to supply both the Stokes and pump photons requires the pulse to have approximately the same phase at all wavelengths (i.e. it must be near transform limited). Dispersion of the pulse must therefore be carefully corrected.

Finally, Lu *et al.* "*Elliptically polarized coherent anti-Stokes Raman scattering microscopy* " *Optics Letters Vol* 33, No. 23, Dec. 1, 2008, describe a CARS microscope which makes use of an elliptically polarised pump field with a specific aspect ratio of $1:\sqrt{3}$ of the ellipse together with a linearly polarised Stokes field. The generated anti-Stokes radiation is then detected at the same polarisation as the Stokes beam. The use of the specific aspect ratio for the elliptical polarisation cancels out non-resonant polarisations, but means that the technique cannot be used when the resonant depolarisation ratio of the Raman-active molecular vibration is equal to ⅓.

SUMMARY OF THE INVENTION

Embodiments of the present invention have arisen out of a project partly concerned with developing a much simpler apparatus for performing CARS. Embodiments of the invention provide a simple and robust system that allows NRB to be removed even when using cheaper laser systems, which do not have transform limited pulses. In particular, resonant CARS signals have a real and imaginary component. The imaginary component is directly related to the spontaneous Raman spectrum, for which there are already large spectral databases to allow chemical identification. The NRB signal, on the other hand, only has a real component. Within embodiments of the invention we therefore wish to recover the imaginary component of the entire CARS signal, and this is done by simultaneously generating two CARS signals at orthogonal polarisations: one has the imaginary components destructively interfering with (i.e. subtracted from) the real components, the other has them constructively interfering. Measuring these two polarisations and subtracting them therefore cancels out the real part of the signal, leaving only the imaginary components.

Within one embodiment of the invention the pump and probe photons are provided by the same laser beam. In order to generate the two orthogonal CARS signals the pump/probe beam, $E_p$, is split into two orthogonal components, one of which is delayed by ¼ wavelength. This is equivalent to elliptically polarising the pump/probe beam, for example by passing it through a λ/4 wave plate. The Stokes beam, $E_s$, is linearly polarised along a given direction, and the anti-Stokes signals generated in the sample and having the orthogonal polarisations are then detected at ±45° to the Stokes beam. The detected anti-Stokes signals are then subtracted one from the other to obtain the imaginary component related to the Raman spectrum.

In another embodiment the pump/probe beam is instead linearly polarised, and the Stokes beam elliptically polarised (and optimally circularly polarised). In such a case anti-Stokes signals generated in the sample have orthogonal polarisations at ±45° to the linearly polarised pump/probe beam. They can then again be subtracted one from the other to obtain the Raman spectrum.

In view of the above, from one aspect the present invention provides a method for reducing a non-resonant background signal obtained during coherent anti-Stokes Raman scattering (CARS) spectroscopy, the method comprising: generating a first beam having a linear polarisation, the first beam being one of a Stokes beam, or a pump/probe beam; generating a second beam having two orthogonal components one of which is delayed by $\lambda/4$ with respect to the other, the second beam being the other of the Stokes beam or the pump/probe beam; directing the Stokes beam and the pump/probe beam at a sample to be characterised, and obtaining two orthogonally polarised anti-Stokes beams therefrom; separating the two orthogonally polarised anti-Stokes beams each having real and imaginary components interfering with each other and detecting the signals thereof; processing the anti-Stokes signals to obtain the imaginary components containing signals related to the Raman spectra of the sample, and to reduce the real components containing the non-resonant background signal.

In a preferred embodiment the second beam is elliptically polarised to provide the two orthogonal components. In particular embodiments the second beam is elliptically polarised such that a major or minor axis of the elliptical polarisation of the second beam is aligned with the polarisation of the first beam, whereby a first orthogonal component of the second beam parallel to the first beam has quadrature phase with respect to a second orthogonal component perpendicular to the first beam.

In one embodiment when the first beam is the Stokes beam and the second beam is the pump/probe beam, the elliptical polarisation is such that the first and second orthogonal components of the elliptical polarisation of the pump/probe beam are each neither equal nor zero. Within this embodiment more preferably the elliptical polarisation is such that the ratio of the first and second orthogonal components of the pump/probe beam is substantially $\tan(\pi/8)$ or substantially $\tan(3\pi/8)$, whereby the imaginary components of the anti-Stokes signals are maximised.

In another embodiment when the first beam is the pump/probe beam and the second beam is the Stokes beam, the elliptical polarisation is such that the first and second orthogonal components of the elliptical polarisation of the Stokes beam are each greater than zero. Within this embodiment the Stokes beam is preferably substantially circularly polarised, whereby the imaginary components of the anti-Stokes signals are maximised.

In embodiments of the invention one of the orthogonally polarised anti-Stokes beams generated in the sample has the real and imaginary components thereof constructively interfering, whereas the other of the orthogonally polarised anti-Stokes beams has the real and imaginary components thereof destructively interfering.

In one embodiment the first and second beam are directed at the sample collinearly.

In a further embodiment the orthogonal anti-Stokes beams are separated using a polarising beam displacer. In another embodiment, the orthogonal anti-Stokes beams are separated using a Wollaston prism.

Furthermore, in some embodiments of the invention the orthogonal anti-Stokes beams are detected using any one or more of the group comprising: a spectrometer and CCD; one or more photomultiplier tubes; one or more avalanche photodiodes; or one or more photodiodes.

In various preferred embodiments of the invention the processing comprises subtracting one orthogonal anti-Stokes signal from the other, whereby to substantially reduce or remove the real component thereof containing the non-resonant background. In particular embodiments the processing further comprises normalising the two signals to account for differences in sensitivity to each polarisation prior to the subtraction.

Finally, in embodiments of the invention the orthogonally polarised anti-Stokes beams are detected at angles of ±45° to the polarisation of the first beam having the linear polarisation. Thus, where the Stokes beam is linearly polarised, the anti-Stokes beams are detected at polarisation angles 45° either side of the polarisation angle of the Stokes beam. Similarly, where the pump/probe beam is linearly polarised, the anti-Stokes beams are detected at polarisation angles 45° either side of the polarisation angle of the pump/probe beam.

From another aspect the invention also provides an apparatus for reducing a non-resonant background signal obtained during coherent anti-Stokes Raman scattering (CARS) spectroscopy, the apparatus comprising: a first beam generating arrangement arranged to generate a first beam having a linear polarisation, the first beam being one of a Stokes beam, or a pump/probe beam; a second beam generating arrangement arranged to generate a second beam having two orthogonal components one of which is delayed by $\lambda/4$ with respect to the other, the second beam being the other of the Stokes beam or the pump/probe beam; a microscope arrangement arranged to direct the Stokes beam and the pump/probe beam at a sample to be characterised, and to obtain two orthogonally polarised anti-Stokes beams therefrom; a beam separator arranged to separate the two orthogonally polarised anti-Stokes beams each having interfering real and imaginary components; a signal detector arranged to detecting the signals of the separated beams; and a signal processor arranged to process the anti-Stokes signals to obtain the imaginary components containing signals related to the Raman spectra of the sample, and to reduce the real components containing the non-resonant background signal.

Within the second aspect the various further features and attendant advantages may also be obtained as explained above in respect of the first aspect.

BRIEF DESCRIPTION OF THE DRAWINGS

Further features and advantages of the present invention will become apparent from the following description of preferred embodiments thereof, presented by way of example only, and by reference to the accompanying drawings, wherein like reference numerals refer to like parts, and wherein.

DESCRIPTION OF THE EMBODIMENTS

The problem that embodiments of the invention solve is the removal of the non-resonant background from CARS signals. They do this through what is essentially an interferometric process. Resonant CARS signals have a real and imaginary component (which is simply a way of saying that one component (real) is generated in phase with the driving fields, while the other (imaginary) is generated in quadrature phase; that is, phase shifted by ¼ wavelength). The spectrum of the resonant part of the real component is 'dispersive' (passes through zero on resonance, with odd symmetry about the resonance), and the imaginary component peaks on resonance, with even symmetry. The imaginary component is directly related to the spontaneous Raman spectrum, for which there are already large spectral databases to allow chemical identification. The NRB signal, on the other hand, only has a real component. The component we wish to recover is therefore the imaginary component of the entire CARS signal.

This is done in embodiments of the invention by simultaneously generating two CARS signals at orthogonal polarisations: one has the imaginary components destructively interfering with (i.e. subtracted from) the real components, the other has them constructively interfering. Measuring these two polarisations and subtracting them therefore cancels out the real part of the signal, leaving only the imaginary components i.e. (Re+Im)−(Re−Im)=2Im.

Figure 3:
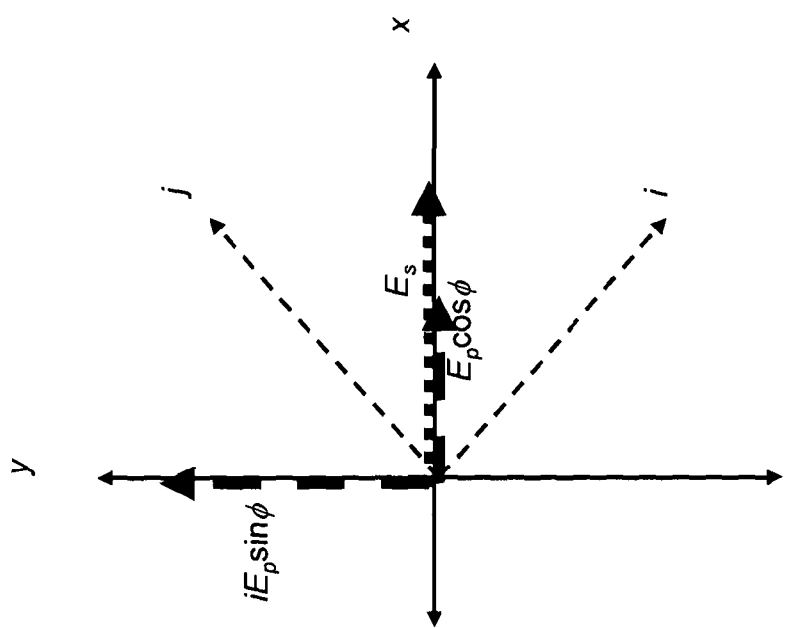
FIG. 3 is a diagram illustrating polarisation orientations of the pump/probe and Stokes beams in the first embodiment.

In a first embodiment to be described, the pump and probe photons are provided by the same narrowband laser beam. In order to generate the two orthogonal CARS signals the pump/probe beam, $E_p$, is split into two orthogonal components, one of which is delayed by ¼ wavelength, as shown in FIG. 3. This is equivalent to elliptically polarising the pump/probe beam $E_p$ by passing it through a λ/4 wave plate. The Stokes beam, $E_s$, is linearly polarised along a given direction, and the anti-Stokes signals are detected at ±45° to the Stokes beam (along i and j in FIG. 3).

Working through the theory, accounting for all possible combinations of polarisations, and using the symmetries of an isotropic medium, gives the result:

$$|E_{as} \cdot \hat{i}|^2 - |E_{as} \cdot \hat{j}|^2 \propto \sin(4\phi) I_p^2 I_s \chi^{nr} \text{Im}\{\chi_{1111}^r - 3\chi_{1212}^r\}$$

Hence, solving from the above the maximum of the imaginary components is achieved for ϕ=67.5° or 22.5°. This condition may can be obtained experimentally by aligning one of the axes of the pump beam's λ/4 plate (described later) with the Stokes beam, and inputting the linearly polarised pump beam to it at ±67.5° or ±22.5° to the Stokes direction. Note that these directions are also equivalent to inputting the pump beam at the angles of ±112.5° and ±157.5°: all orientations that generate the required ellipticities are therefore implied. Optics between the polarisation optics and the objective lens also alter the polarisation state of the fields: In the present arrangement to be described, the wave plates and polarisers are therefore orientated in such a way as to compensate for these effects, so that the polarisation state at the focus is as required (i.e. as shown in FIG. 3). Note that the term $\chi_{1111}^r - 3\chi_{1212}^r$ is typically non-zero at a vibrational resonance. Also note that this term is amplified by the non-resonant background, $\chi^{nr}$, and is linear in $\chi^r$. The real components along i and j are smaller for the case of ϕ=67.5°, hence this configuration is expected to give better signal-to-noise than for ϕ=22.5°, as the real part of the signal will contribute less shot noise.

Figure 1:
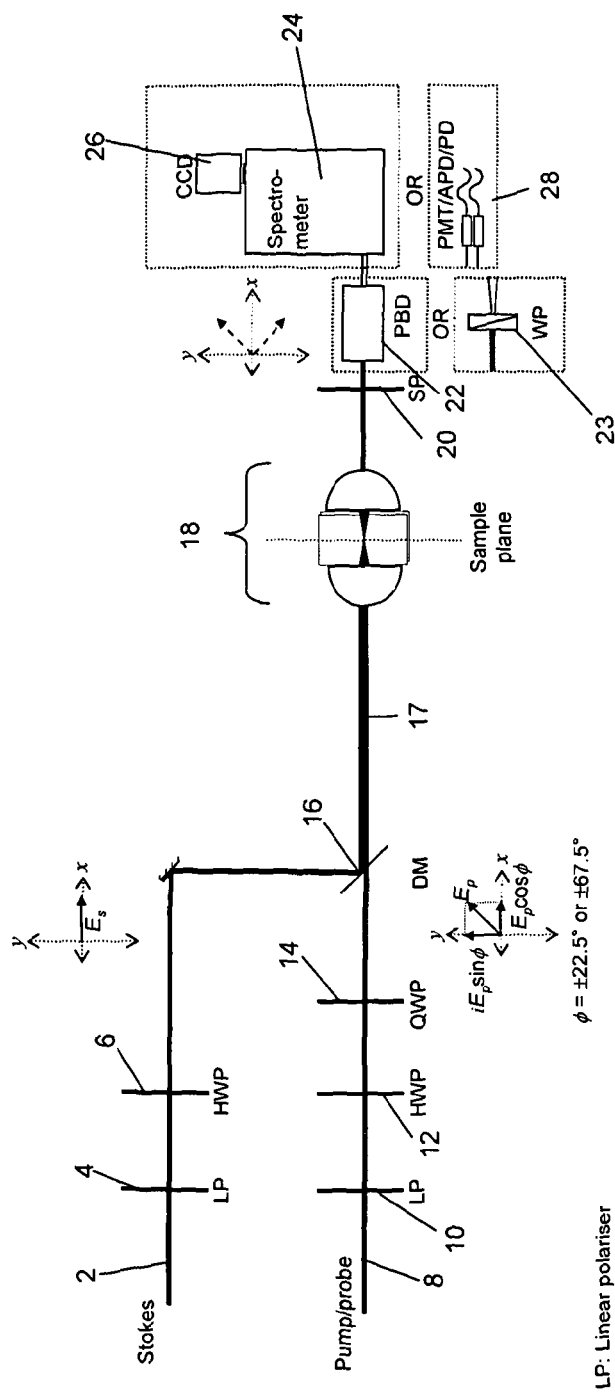
FIG. 1 is an optical circuit diagram of a first embodiment of the invention.

In terms of the optical circuit to produce the above noted required polarisation conditions, FIG. 1 illustrates an example optical circuit to provide a CARS microscope according to the present embodiment.

As shown in FIG. 1, the first embodiment of the invention consists of a laser source (not shown), a particular arrangement of polarisation optics, focusing lenses, and a detector. The laser should be capable of generating synchronised pulses of at least two different wavelengths: the current embodiment uses a system that has a broadband laser pulse (consisting of a wide range of wavelengths) synchronised with a narrowband (approximately single wavelength) output. However the pulses are generated, they are ultimately formed into two pulse trains, one of which is narrowband and of higher energy than the other. The higher energy pulses are called the pump/probe beam, while the lower energy ones constitute the Stokes beam.

As shown in FIG. 1, in the present embodiment a laser source (not shown) having the characteristics discussed previously is used to generate the Stokes beam 2. The Stokes beam 2 is linearly polarised along a particular direction; this is done by passing the beam through a λ/2 wave plate 6 (HWP) and a linear polariser 4 (LP) (which can be arranged in either order). We choose our coordinate system such that the x-axis is along direction of polarisation of the Stokes beam, and the beams are propagating along the z-axis. The laser source also produces the pump/probe beam 8, having the characteristics discussed previously. The pump/probe beam 8 is formed into an elliptically polarised beam, with a particular ellipticity and orientation with respect to the Stokes beam. In particular, in this embodiment the pump/probe beam 8 has an ellipticity of approximately +π/8 or −π/8 radians, with the semi-major axis either oriented along the x-axis (ϕ=±22.5°), or orientated along the y-axis (ϕ=±67.5°). This is done via passing the beam 8 through a linear polariser 10 (LP) and λ/2 plate 12 (HWP), followed by a λ/4 plate 14 (QWP). As discussed previously, the desired elliptical polarisation condition may can be obtained experimentally by aligning one of the axes of the pump beam's λ/4 plate (described later) with the Stokes beam, and inputting the linearly polarised pump beam to it at ±67.5° or ±22.5° to the Stokes direction.

At this point, therefore, the Stokes beam 2 is linearly polarised, with the direction of linear polarisation defining the coordinate system x-axis, and the pump/probe beam is elliptically polarised, having its major axis parallel or perpendicular to the Stokes beam, and an ellipticity of ±22.5°, to obtain maximal imaginary components of the anti-Stokes signal at the output. As will be discussed further later, in less optimal embodiments other polarisation angles may be used, although the imaginary components of the anti-Stokes signal will not be maximised.

CARS is an interferometric mixing process wherein the pump/probe beams and the Stokes beam interact in the sample being imaged and induce a coherent radiation source having a third-order nonlinear polarisation. Further details of the physical processes behind CARS are apparent from the review paper Vollmer, A, *Vibrational imaging and microspectroscopies based on coherent anti-Stokes Raman scattering microscopy* J. Phys. D: Appl. Phys. vol 38 (2005) R.59-R81. In order to provide such mixing in the present embodiment the pump/probe beam 8 and the Stokes beam 2 are mixed together on a suitable dichroic filter 16 such that they are collinear. The dichroic filter 16 should have a transition wavelength between the pump and Stokes wavelengths, and can either be a longpass pass or shortpass filter (this distinction merely changes the direction that the collinear beams emerge).

Having obtained collinear beams (17), the collinear beams are then focused by suitable microscope optics 18 into the sample of interest, and resultant light (which now contains the CARS signal) is collected by another microscope lens, and the driving fields are filtered out via a shortpass filter 20 (SP). It should be noted here that in order to obtain a two dimensional microscopic image the collinear beams are preferably raster scanned across the area of the sample, either by suitable controlled optics (i.e. gimbaled mirrors), or by moving the sample within the beam, or a combination of the two.

After filtering by the shortpass filter 20, the remaining light is then passed through a polarising beam displacer 22 (PBD) or polarisation deviating prism, such as a Wollaston prism 23 (WP), orientated such that it splits the polarisation at $\pm\pi/4$ radians to the Stokes beam polarisation. These two orthogonal polarisations are then imaged onto a detector. In the present embodiment, they are dispersed by a spectrometer 24 and imaged onto a CCD detector 26; however in other embodiments with narrowband Stokes beams they could instead be imaged onto point detectors 28, such as photomultiplier tubes (PMT's) or avalanche photodiodes (APD's).

Recall here that the two CARS signals having the two orthogonal polarisations have the properties that one of the polarisations has the imaginary components destructively interfering with (i.e. subtracted from) the real components, and the other polarisation has them constructively interfering. Therefore, the two detected signals representing the two polarisations once captured are processed, for example by a computer running appropriate software (not shown). The processing applied comprises multiplying each captured signal representing one of the generated CARS polarisations by a factor to account for differences in sensitivity to each polarisation to thereby produce normalised signals, and then subtracting one of the normalised signals from the other to cancel the real component and retain the imaginary component containing the Raman spectrum. The obtained Raman spectrum can then be compared against a database of known Raman spectra to provide chemical and physical structure information relating to the sample.

The main advantages of embodiments of the invention are their simplicity, robustness, and that they make it possible to measure NRB corrected CARS signals with much simpler and less expensive laser systems than has heretofore been the case. For example broad spectrum super continuum lasers may be used, and in particular those based on photonic crystal fibre.

More specifically, extremely spectrally broad pulses can be created by passing a short laser pulse through a photonic crystal fibre (PCF). This is technically a much simpler process than generating or temporally compressing an ultra-short pulse, and relatively cheap commercial systems are now available. However, the resultant pulse is not transform limited, and therefore existing interferometric NRB removal techniques cannot be applied to it. Embodiments of the invention make it possible to remove NRB from CARS generated by such pulses, using only simple optics. This is possible because the interference that is detected is essentially between signals generated by the same beam, merely shifted by ¼ wavelength, and following identical paths. Despite its simplicity, embodiments of the invention maintain the advantages of other systems; namely, homodyne amplification of the imaginary component of the third order CARS response.

Various modifications may be made to the above described embodiment to produce further embodiments.

For example, in some embodiments, depending on the polarisation state generated in the source some of the polarisation optics such as the linear polarisers, half wave plate, or quarter wave plate may not be necessary. What is important in the present embodiment is the relative polarisations of the beams i.e. that the Stokes beam is linearly polarised, and the pump/probe beam is elliptically polarised, as it is the elliptical polarisation that results in the orthogonal CARS signals at the output. Moreover, by choosing the correct polarisation angles, the imaginary component of the CARS signals can be maximised In this respect more generally the present embodiment of the invention involves making the component of the pump/probe beam parallel to the Stokes beam have quadrature phase with respect to the component perpendicular to the Stokes beam. This requires that the major or minor axis of the elliptical polarisation of the pump/probe beam is aligned with the Stokes polarisation. The amplitude of the components of the pump/probe beam can not be equal and neither can be zero; the optimum ratio of amplitudes being $\tan(\pi/8)$ and $\tan(3\pi/8)$.

In this latter respect, as noted in the above embodiment an ellipticity angle $\phi$ of $\pm 22.5°$ or $\pm 67.5°$ is used (measured against the direction of linear polarisation of the Stokes beam), as these values maximise the imaginary component in the orthogonal CARS signals at the output. Whilst this is preferred, in less preferred embodiments different angles may be used, although with an attendant reduction in the imaginary component obtained, and hence a reduction in signal to noise ratio in the output signal. At example outer limits, $\phi$ may take values between the ranges substantially $\pm 2.5°$ to substantially $\pm 42.5°$ and substantially $\pm 47.5°$ to substantially $\pm 87.5°$ (i.e. 20° either side of the maximal values) or more preferably within 10° either side of the maximal values (i.e. between the ranges substantially $\pm 12.5°$ to substantially $\pm 32.5°$ and substantially $\pm 57.5°$ to substantially $\pm 77.5°$), or more preferably within 5° either side of the maximal values (i.e. between the ranges substantially $\pm 17.5°$ to substantially $\pm 27.5°$ and substantially $\pm 62.5°$ to substantially $\pm 72.5°$), or even more preferably within 2° either side of the maximal values (i.e. between the ranges substantially $\pm 20.5°$ to substantially $\pm 24.5°$ and substantially $\pm 65.5°$ to substantially $\pm 69.5°$). Ideally however, the arrangement should be such that the angle is substantially $\pm 22.5°$ or $\pm 67.5°$ as discussed, as these angles lead to a maximised imaginary component. As $\phi$ varies from these angles, the imaginary component is reduced. At 20° to one side of one of the maximal angles the imaginary component in the orthogonal anti-Stokes beams is only 17% of the maximum.

In addition, within further embodiments, and depending on the polarisation state of the laser source, there are alternative ways to generate the particular polarisation states that the method requires—for example, via a spatial light modulator—however this is more complicated and requires more expensive equipment than the preferred embodiment described.

In the above described embodiment a dichroic mirror is used to direct the polarised pump/probe beams and Stokes beam at the sample in a collinear fashion. In other embodiments a beam splitter or a notch filter may be used.

Alternative embodiments may also differ in the way that the orthogonal signal polarisations are detected. In one embodiment the two measurements may be taken sequentially with different orientations of a linear polariser, although the embodiment described above where a polarising beam displacer or Wollaston prism is used to separate the signals onto a CCD camera is more advantageous as both the signals can be acquired in a single shot. Other types of polarising optics, such as Nomarski prisms, Nicol prisms, polarising beam splitters, etc. may also be used to separate out the two orthogonal signal polarisations.

In another embodiment a single broadband source such as a supercontinuum laser may be used to generate the pump/probe and Stokes beams. In such a case the operation of such an embodiment is identical to that described above in that a beam having orthogonal components is needed to generate the two orthogonally polarised CARS output beams, and hence the operating concepts of the embodiments are also applicable to "single beam" CARS apparatus.

In other embodiments narrowband laser sources may be used, which would give a NRB-free measurement of the CARS signal at a single wavelength. This is a trivial simplification of the broadband case we have already implemented, and indicates that the invention is applicable to existing narrowband CARS systems.

In one particular alternative embodiment to the above, instead of the pump/probe beam being elliptically polarised, the Stokes beam can instead be elliptically polarised, and the pump/probe beams linearly polarised along a given direction. The CARS signal fields are then detected at polarisations orientated at $\pm\pi/4$ radians to the polarisation of the pump/probe beams. In this instance the CARS signal is given by:

$$|E_{as}\cdot\hat{i}|^2 - |E_{as}\cdot\hat{j}|^2 \propto \sin(2\phi) I_p^2 I_s \chi''' \operatorname{Im}\{\chi_{1111}{}' - 3\chi_{1212}{}'\}$$

In this embodiment the components of the Stokes beam along the directions parallel and perpendicular to the pump/probe beams should have quadrature phase with respect to each other. Note also the $\sin(2\phi)$ prefactor; hence neither of these components can be zero, and the optimum signal is obtained when the components are of equal magnitude (i.e. the Stokes beam is circularly polarised). Such an arrangement is not as well suited to the situation of a broadband Stokes beam, as giving a broadband beam the same elliptical polarisation at every wavelength is experimentally difficult (though nevertheless possible). It is, however, simple to implement in the case of narrowband Stokes beams.

In terms of the optical circuit required, the same optical circuit as shown in FIG. 1 may be used, although with the Stokes and pump/probe beam sources swapped around (particularly with a narrowband Stokes beam source). That is, beam 2 becomes the linearly polarised pump/probe beam, and beam 8 the elliptically polarised (optimally circularly polarised) Stokes beam. Usually, in order to obtain a circularly polarised Stokes beam, the quarter wave plate 14 is set to an angle of 45° to the incident light.

Both of the main embodiments of the invention (i.e. the first embodiment with the Stokes beam linearly polarised, or the alternative embodiment with the pump/probe beam linearly polarised) can also be applied to arrangements where the pump and probe beams have different frequencies (non-degenerate CARS), and arrangements where the beams are not collinear (such as BOXCARS and widefield CARS). For non-collinear arrangements, the polarisations are adjusted such that they have the polarisation conditions specified above in the plane orthogonal to the direction of propagation of the generated anti-Stokes beam.

The operating concepts of embodiments of the invention may also have additional applications outside CARS microscopy. In this respect, it is a general result that an oscillator driven on resonance oscillates in quadrature to the driving field. So, the operating concepts of the described embodiments of the invention could in principle be applied in other embodiments to any third-order interaction involving electromagnetic fields.

In particular, in other embodiments of the invention the operating concept of the embodiments whereby elliptical polarisation in the pump/probe beam or Stokes beam is used to cause the quadrature field to interact oppositely with orthogonal polarisations from a third order coherent mixing process has application to other areas that employ CARS, and which suffer from non-resonant background—for example; combustion diagnostics, stand-off detection of trace amounts of solids, surface-enhanced CARS (SECARS), and almost any form of CARS microscopy. In addition, techniques that use spontaneous Raman scattering, such as semiconductor wafer inspection, may also be areas of application in that the operating concept allows for measurement of the same properties as spontaneous Raman scattering (i.e. the imaginary component of the third order response). However, the CARS process is orders of magnitude stronger, hence the focus herein on CARS applications.

Figure 2:
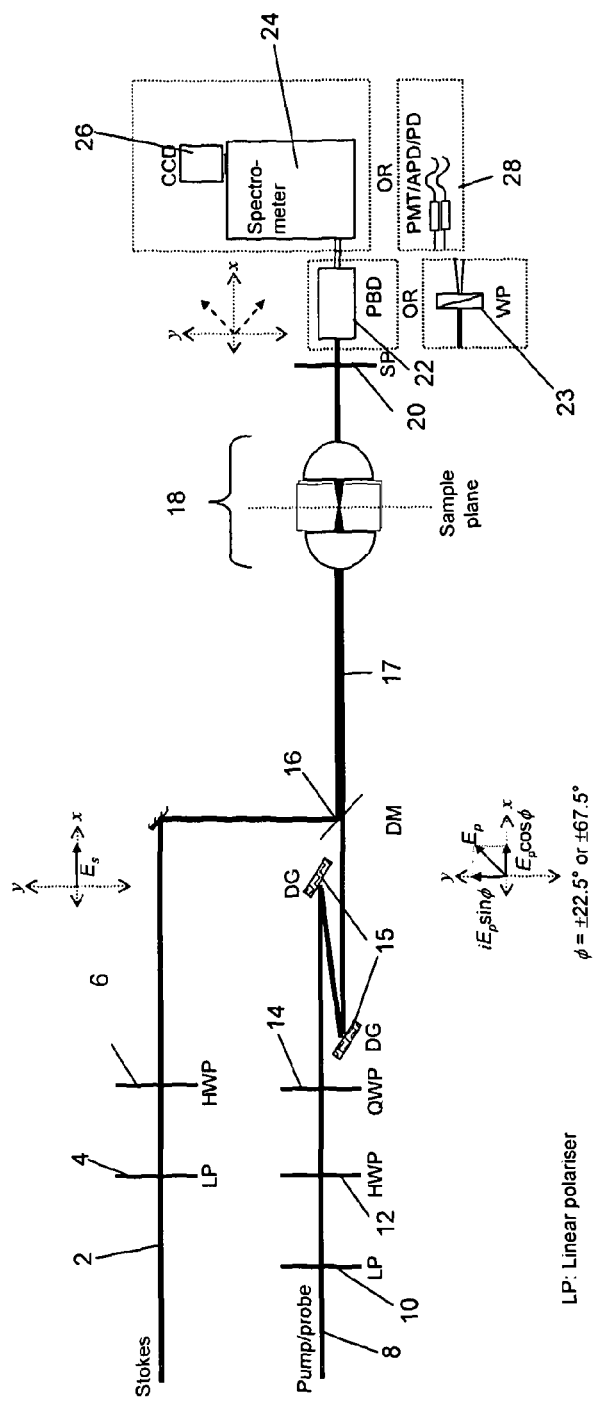
FIG. 2 is an optical circuit diagram of a second embodiment of the invention.

As a further modification to provide an additional embodiment, the pump beam can be chirped such that the different wavelengths constituting the pulse become temporally spread out. This can increase the duration that the pump pulse overlaps the Stokes pulse if it too has some chirp or is of a longer duration, and thereby increase the signal. Also, chirping the pump beam lowers its instantaneous spectral width and thereby improves the spectral resolution of the anti-Stokes signal. Pulses can be chirped by combining dispersive optical elements such as diffraction gratings, prisms, chirped mirrors, or grisms, or by simply passing through a sufficient amount of a dispersive medium, such as glass. FIG. 2 illustrates a further embodiment where chirping is performed by a pair of identical gratings 15; the first grating spectrally disperses the pulse, and the second grating recollimates the wavelengths of the pulse, such that each wavelength has traversed a different path length to the others. Other than the addition of the pair of diffraction gratings 15, the configuration and operation of the embodiment of FIG. 2 is identical to FIG. 1, previously described.

Further modifications whether by way of addition, deletion or substitution will be apparent to the above described embodiments to produce further embodiments any and all of which are intended to be encompassed by the appended claims.

The invention claimed is:

1. A method for reducing a non-resonant background signal obtained during coherent anti-Stokes Raman scattering (CARS) spectroscopy, the method comprising:
    generating a first beam having a linear polarisation, the first beam being one of a Stokes beam, or a pump/probe beam;
    generating a second beam having two orthogonal components one of which is delayed by $\lambda/4$ with respect to the other, the second beam being the other of the Stokes beam or the pump/probe beam;
    directing the Stokes beam and the pump/probe beam at a sample to be characterised, and obtaining two orthogonally polarised anti-Stokes beams therefrom;
    separating the two orthogonally polarised anti-Stokes beams each having real and imaginary components interfering and detecting the signals thereof;
    processing the anti-Stokes signals to obtain the imaginary components containing signals related to the Raman spectra of the sample, and to reduce the real components containing the non-resonant background signal.

2. A method according to claim 1, wherein the second beam is elliptically polarised to provide the two orthogonal components.

3. A method according to claim 2, wherein the second beam is elliptically polarised such that a major or minor axis of the elliptical polarisation of the second beam is aligned with the linear polarisation of the first beam, whereby a first orthogonal component of the second beam parallel to the first beam has quadrature phase with respect to a second orthogonal component perpendicular to the first beam.

4. A method according to claim 3, wherein when the first beam is the Stokes beam and the second beam is the pump/ probe beam, the elliptical polarisation is such that the first and second orthogonal components of the elliptical polarisation of the pump/probe beam are each neither equal nor zero.

5. A method according to claim 4, wherein the elliptical polarisation is such that the ratio of the first and second orthogonal components of the pump/probe beam is substantially $\tan(\pi/8)$ or substantially $\tan(3\pi/8)$, whereby the imaginary components of the anti-Stokes signals are maximised.

6. A method according to claim 3, wherein when the first beam is the pump/probe beam and the second beam is the Stokes beam, the elliptical polarisation is such that the first and second orthogonal components of the elliptical polarisation of the Stokes beam are each greater than zero; and
wherein, optionally, the Stokes beam is substantially circularly polarised, whereby the imaginary components of the anti-Stokes signals are maximised.

7. A method according to claim 1, wherein the first and second beam are directed at the sample collinearly.

8. A method according to claim 1, wherein the orthogonal anti-Stokes beams are separated using a polarising beam displacer or a Wollaston prism.

9. A method according to claim 1, wherein the orthogonal anti-Stokes beams are detected using at least one of the group consisting of: a spectrometer and CCD; one or more photomultiplier tubes; one or more avalanche photodiodes; and one or more photodiodes.

10. A method according to claim 1, wherein the processing comprises subtracting one orthogonal anti-Stokes signal from the other, whereby to substantially reduce or remove the real component thereof containing the non-resonant background; and
wherein, optionally, the processing further comprises normalising the two signals to account for differences in sensitivity to each polarisation prior to the subtraction.

11. A method according to claim 1, further comprising chirping the pump/probe beam.

12. A method according to claim 1, wherein the orthogonally polarised anti-Stokes beams are detected at angles of ±45° to the polarisation of the first beam having the linear polarisation.

13. An apparatus for reducing a non-resonant background signal obtained during coherent anti-Stokes Raman scattering (CARS) spectroscopy, the apparatus comprising:
a first beam generating arrangement arranged to generate a first beam having a linear polarization, the first beam being one of a Stokes beam, or a pump/probe beam;
a second beam generating arrangement arranged to generate a second beam having two orthogonal components one of which is delayed by $\lambda/4$ with respect to the other, the second beam being the other of the Stokes beam or the pump/probe beam;
a microscope arrangement arranged to direct the Stokes beam and the pump/probe beam at a sample to be characterized, and to obtain two orthogonally polarized anti-Stokes beams therefrom;
a beam separator arranged to separate the two orthogonally polarized anti-Stokes beams each having real and imaginary components;
a signal detector arranged to detect the signals of the separated beams;
and a signal processor arranged to process the anti-Stokes signals to obtain the imaginary components containing signals related to the Raman spectra of the sample, and to reduce the real components containing the non-resonant background signal.

14. An apparatus according to claim 13, wherein the second beam is elliptically polarised to provide the two orthogonal components.

15. An apparatus according to claim 13, wherein the second beam is elliptically polarised such that a major or minor axis of the elliptical polarisation of the second beam is aligned with the linear polarisation of the first beam, whereby a first orthogonal component of the second beam parallel to the first beam has quadrature phase with respect to a second orthogonal component perpendicular to the first beam.

16. An apparatus according to claim 15, wherein when the first beam is the Stokes beam and the second beam is the pump/probe beam, the elliptical polarisation provided by the second beam generation arrangement is such that the first and second orthogonal components of the elliptical polarisation of the pump/probe beam are each neither equal nor zero.

17. An apparatus according to claim 16, wherein the elliptical polarisation is such that the ratio of the first and second orthogonal components of the pump/probe beam is substantially $\tan(\pi/8)$ or substantially $\tan(3\pi/8)$, whereby the imaginary components of the anti-Stokes signals are maximised.

18. An apparatus according to claim 15, wherein when the first beam is the pump/probe beam and the second beam is the Stokes beam, the elliptical polarisation provided by the second beam generation arrangement is such that the first and second orthogonal components of the elliptical polarisation of the Stokes beam are each greater than zero;
wherein, optionally, the second beam generation arrangement substantially circularly polarises the Stokes beam, whereby the imaginary components of the anti-Stokes signals are maximised.

19. An apparatus according to claim 13, and further comprising beam directing means arranged to direct the first and second beams at the sample collinearly;
wherein, optionally, the beam directing means comprises a dichroic mirror.

20. An apparatus according to claim 13, wherein the beam separator is a polarising beam displacer or a Wollaston prism.

21. An apparatus according to claim 13, wherein the orthogonal anti-Stokes beams are detected using at least one of the group consisting of: a spectrometer and CCD; one or more photomultiplier tubes; one or more avalanche photodiodes; and one or more photodiodes.

22. An apparatus according to claim 13, wherein the signal processor is further arranged to subtract one orthogonal anti-Stokes signal from the other, whereby to substantially reduce or remove the real component thereof containing the non-resonant background;
wherein, optionally, the signal processor is further arranged to normalise the two signals to account for differences in sensitivity to each polarisation prior to the subtraction.

23. An apparatus according to claim 13, wherein the orthogonally polarised anti-Stokes beams are detected at angles of ±45° to the polarisation of the first beam having the linear polarization.

24. An apparatus according to claim 13, and further comprising a chirping means, such as a dispersive optical element or medium, arranged in the path of the pump/probe beam to chirp the pump/probe beam.

* * * * *